(12) United States Patent
Cise

(10) Patent No.: US 6,629,530 B2
(45) Date of Patent: Oct. 7, 2003

(54) SINGLE-ELEMENT SEALING VALVE FOR A RESPIRATORY SUPPORT SYSTEM

(75) Inventor: David M. Cise, Herriman, UT (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 109 days.

(21) Appl. No.: 09/748,297

(22) Filed: Dec. 22, 2000

(65) Prior Publication Data
US 2002/0078960 A1 Jun. 27, 2002

(51) Int. Cl.$^7$ .................................................. A62B 9/02
(52) U.S. Cl. .............................. 128/205.24; 128/207.15
(58) Field of Search ...................... 128/205.19, 205.24, 128/207.14–207.18, DIG. 26, 912, 202.27; 604/256, 533; 137/907, 908, 315.07, 315.11, 843, 844

(56) References Cited

U.S. PATENT DOCUMENTS

| | | | | |
|---|---|---|---|---|
| 4,193,406 A | * | 3/1980 | Jinotti .................... | 128/204.18 |
| 4,351,328 A | | 9/1982 | Bodai | |
| 4,475,548 A | | 10/1984 | Muto | |
| 4,960,412 A | | 10/1990 | Fink | |
| 5,197,463 A | * | 3/1993 | Jeshuran ................ | 128/207.14 |
| 5,342,315 A | * | 8/1994 | Rowe et al. ........... | 604/167.06 |
| 5,343,857 A | * | 9/1994 | Schneider et al. ..... | 128/200.23 |
| 5,360,417 A | * | 11/1994 | Gravener et al. ........... | 604/278 |
| 5,429,609 A | * | 7/1995 | Yoon ..................... | 604/167.03 |
| 5,545,142 A | * | 8/1996 | Stephens et al. ....... | 604/167.01 |
| 5,582,161 A | * | 12/1996 | Kee ....................... | 128/200.26 |
| 5,598,840 A | | 2/1997 | Iund et al. | |
| 5,709,664 A | * | 1/1998 | Vandenbroek et al. . | 604/167.04 |
| 5,727,770 A | * | 3/1998 | Dennis ................... | 251/149.1 |
| 5,735,271 A | | 4/1998 | Lorenzen et al. | |
| 5,738,091 A | | 4/1998 | Kee et al. | |
| 5,746,199 A | * | 5/1998 | Bayron et al. ......... | 128/205.24 |
| 5,752,938 A | * | 5/1998 | Flatland et al. ........ | 604/167.01 |
| 5,775,325 A | | 7/1998 | Russo | |
| 5,779,672 A | | 7/1998 | Dormandy, Jr. | |
| 5,782,817 A | * | 7/1998 | Franzel et al. .............. | 604/256 |
| 5,791,337 A | | 8/1998 | Coles et al. | |
| 5,814,026 A | * | 9/1998 | Yoon ............................ | 604/539 |
| 5,843,046 A | * | 12/1998 | Motisi et al. ............... | 604/256 |
| 5,989,233 A | * | 11/1999 | Yoon ............................ | 604/523 |
| 6,227,200 B1 | * | 5/2001 | Crump et al. .......... | 128/207.14 |
| 6,258,065 B1 | * | 7/2001 | Dennis et al. ......... | 604/167.01 |
| 6,344,033 B1 | * | 2/2002 | Jepson et al. ............... | 128/912 |
| 6,415,788 B1 | * | 7/2002 | Clawson et al. ....... | 128/201.13 |
| 6,416,499 B2 | * | 7/2002 | Paul, Jr. ...................... | 604/256 |

FOREIGN PATENT DOCUMENTS

| | | |
|---|---|---|
| DE | 3737121 A1 | 5/1989 |
| DE | 3737121 | * 11/1989 |
| WO | WO 9958186 | 11/1999 |
| WO | WO 99/58186 | * 11/1999 |

* cited by examiner

Primary Examiner—Weilun Lo
Assistant Examiner—Teena Mitchell
(74) Attorney, Agent, or Firm—Dority & Manning, P.A.

(57) ABSTRACT

An access port closure valve for use with a respiratory support system is provided. The access port closure valve has a sealing member that has a first and second sealing lip. The sealing lips are elongated and are parallel to one another. The sealing lips are at least partially cylindrical in shape and are urged against one another to form a seal that has a taper. An elongated cylindrical frame substantially surrounds the sealing member. The sealing lips are disposed transversely across an end of the frame. The frame is configured to engage the respiratory support system. The sealing member seals the frame and accommodates passage of a surgical instrument through the valve.

21 Claims, 5 Drawing Sheets

SINGLE-ELEMENT SEALING VALVE FOR A RESPIRATORY SUPPORT SYSTEM

TECHNICAL FIELD

This invention relates generally to a respiratory support system, and more particularly to an access port closure valve for use with a respiratory support system.

BACKGROUND

Respiratory support systems are frequently used for the ventilation of critically ill patients. In most instances, the respiratory support system includes an artificial airway such as a tracheal tube positioned either directly in the trachea or through the nose or mouth into the trachea of a patient. A multi-port manifold is connected to the tracheal tube at one port position of the manifold. A source of oxygen is connected to the manifold at a second port thereof. The respiratory support system assists the patient in maintaining adequate blood oxygenation levels without straining the patient's heart and lungs.

Because the patient can no longer clear his or her airway through coughing and other natural functions, it is periodically necessary to aspirate fluids from the patient's trachea or lungs. In the past, in order to accomplish aspiration within certain types of respiratory systems, it has been necessary to disassemble part of the respiratory system by removing the ventilator manifold or by opening a port in the manifold and inserting a small diameter suction catheter tube down the tracheal tube and into the patient's trachea and lungs. The fluid is suctioned from the patient, the suction catheter is removed, and the respiratory support system is reassembled.

However, due to the interruption of respiratory support during this procedure, a patient's blood oxygen level could drop to an unacceptable level. One solution to this problem is to provide a ventilator or manifold that has an access port that is normally sealed but through which a suction catheter could be inserted. Such an access port allows for the insertion of a catheter and aspiration of the patient without a drop in positive end expiratory pressure (PEEP). Once aspiration of the patient is complete, the catheter can be removed from the tracheal tube and manifold without having to detach or reassemble the manifold. This is because the access port will seal automatically once the catheter is removed. Such an access port is described in U.S. Pat. No. 4,351,328 issued to Bodai.

The present invention is an improvement on access ports that allow for the aspiration of patients without a drop in PEEP.

SUMMARY

Objects and advantages of the invention will be set forth in part in the following description, or may be obvious from the description, or may be learned from practice of the invention.

The present invention provides for an improved sealing port on a manifold that can be used with not only a catheter, but with other respiratory instrumentation. Examples of such include lavage and instrumentation to monitor and view the tracheal and respiratory path.

The access port closure valve according to the invention includes a sealing member having a first and second sealing lip. The sealing lips may be elongated and are parallel to one another. The sealing lips are at least partially cylindrical in shape and are urged against one another to form a tapered seal.

The access port closure valve may also include an elongated cylindrical frame that substantially surrounds the sealing member, the first and second sealing lips disposed transversely in the cylindrical frame. The frame is configured to engage the respiratory support system. The sealing member seals the frame, and the frame accommodates passage of a surgical instrument through one end of the frame to the other.

The present invention also encompasses a respiratory support system that includes a manifold having at least one port. An access port closure valve engages the port on the manifold and may include a sealing member as discussed above. Also, the access port closure valve may include an elongated frame as discussed above, wherein the frame is configured to engage the manifold port.

Alternatively, the above-identified embodiments of the present invention can further include a plurality of biasing members. These biasing members may be located on each sealing lip and contribute to the at least partially cylindrical shape of the first and second sealing lips.

In one embodiment of the access port closure valve, the sealing member and the elongated cylindrical frame are a single integral part and are made from the same material.

BRIEF DESCRIPTION OF THE DRAWINGS

FIG. 4A shows the access port closure valve in a closed sealed position and FIG. 4B shows the valve in a closed sealed position with a suction catheter inserted therethrough.

DETAILED DESCRIPTION

Figure 1:
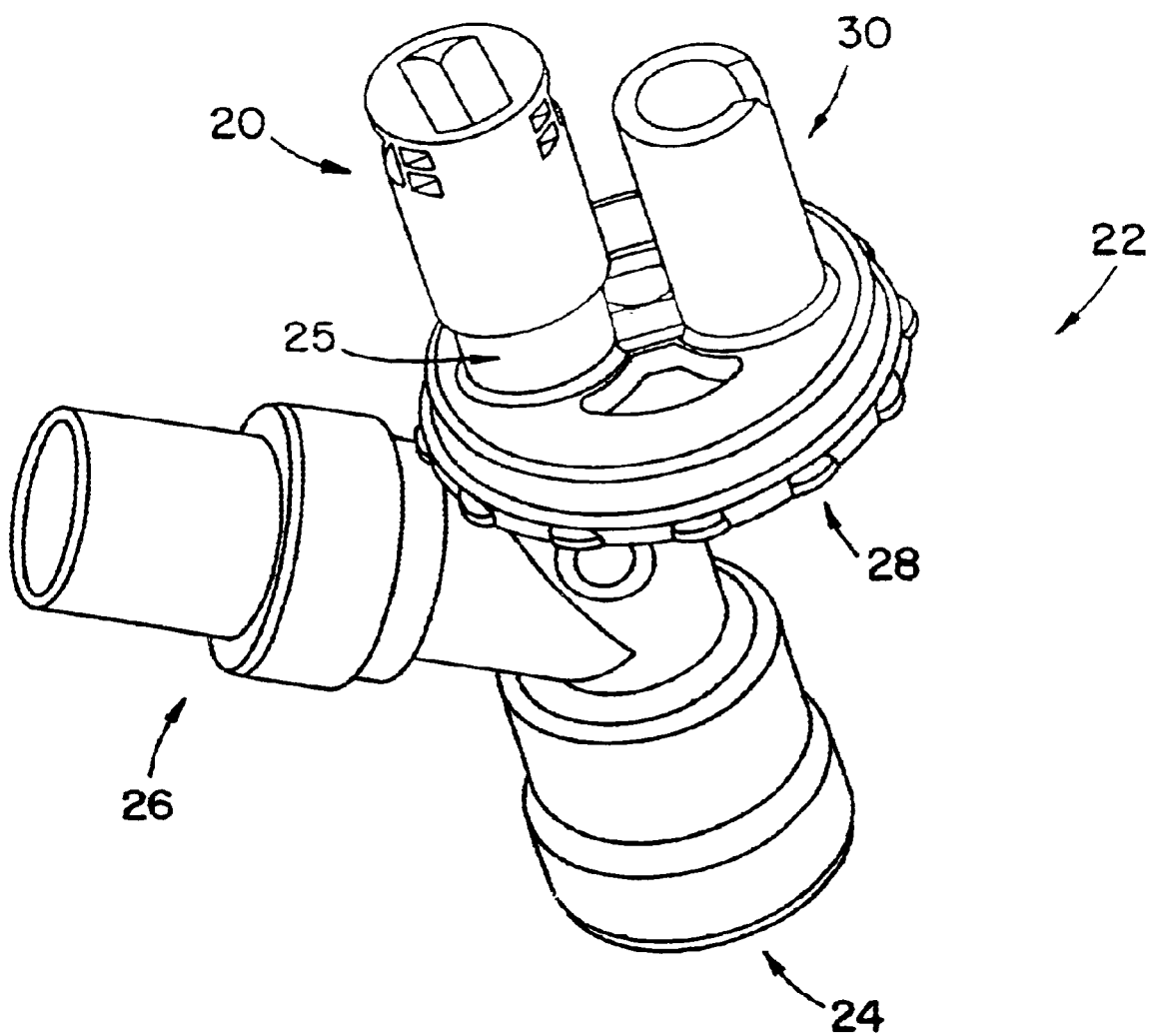
FIG. 1 is a perspective view of an access port closure valve of the present invention incorporated with a manifold that is used in a respiratory support system.

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

Referring now to the drawings, FIG. 1 shows an access port closure valve, generally 20, for use with a respiratory support system. The access port closure valve 20 is shown attached to a manifold 22 of a ventilation circuit. The manifold 22 has an aspiration and ventilation port 24 that is attachable to the proximal end of a tracheal tube (not shown), and a ventilation port 26 that is attachable to a source of respiratory air. Various types and configurations of respiratory system manifolds are known to those skilled in the art and a detailed description of the construction and operation of the manifold 22 is not necessary for an understanding of the closure valve 20. The manifold 22 has a rotatable member 28 that can move the first access port 25 and the second access port 30 into and out of alignment with the aspiration and ventilation port 24. The manifold 22 shown in FIG. 1 is described in detail in commonly owned U.S. Pat. No. 5,735,271 incorporated herein by reference in its entirety for all purposes.

The access port closure valve 20 is shown attached to the first access port 25. Bronchoscopes, catheters, sensor devices, or other medical instruments can be introduced into the airway of a patient by insertion through the access port closure valve 20, the first access port 25, and then through the aspiration and ventilation port 24. The manifold 22 is provided with the second access port 30 shown in a closed position in FIG. 1. Upon rotation of the manifold 22, the second access port 30 can be moved into an open or aligned position with respect to the port 24 and access to the tracheal path can now be obtained through the second access port 30. It is to be understood that the access port closure valve 20 can be used on either or both first access port 25 or second access port 30 and such embodiments are considered to be within the scope of the present invention.

The use of the access port closure valve 20 on the manifold 22 prevents a drop in PEEP because the manifold 22 is sealed before, during, and after insertion of a medical instrument into the airway of a patient through the valve. The use of the access port closure valve 20 also reduces contamination to and from a patient.

Figure 2:
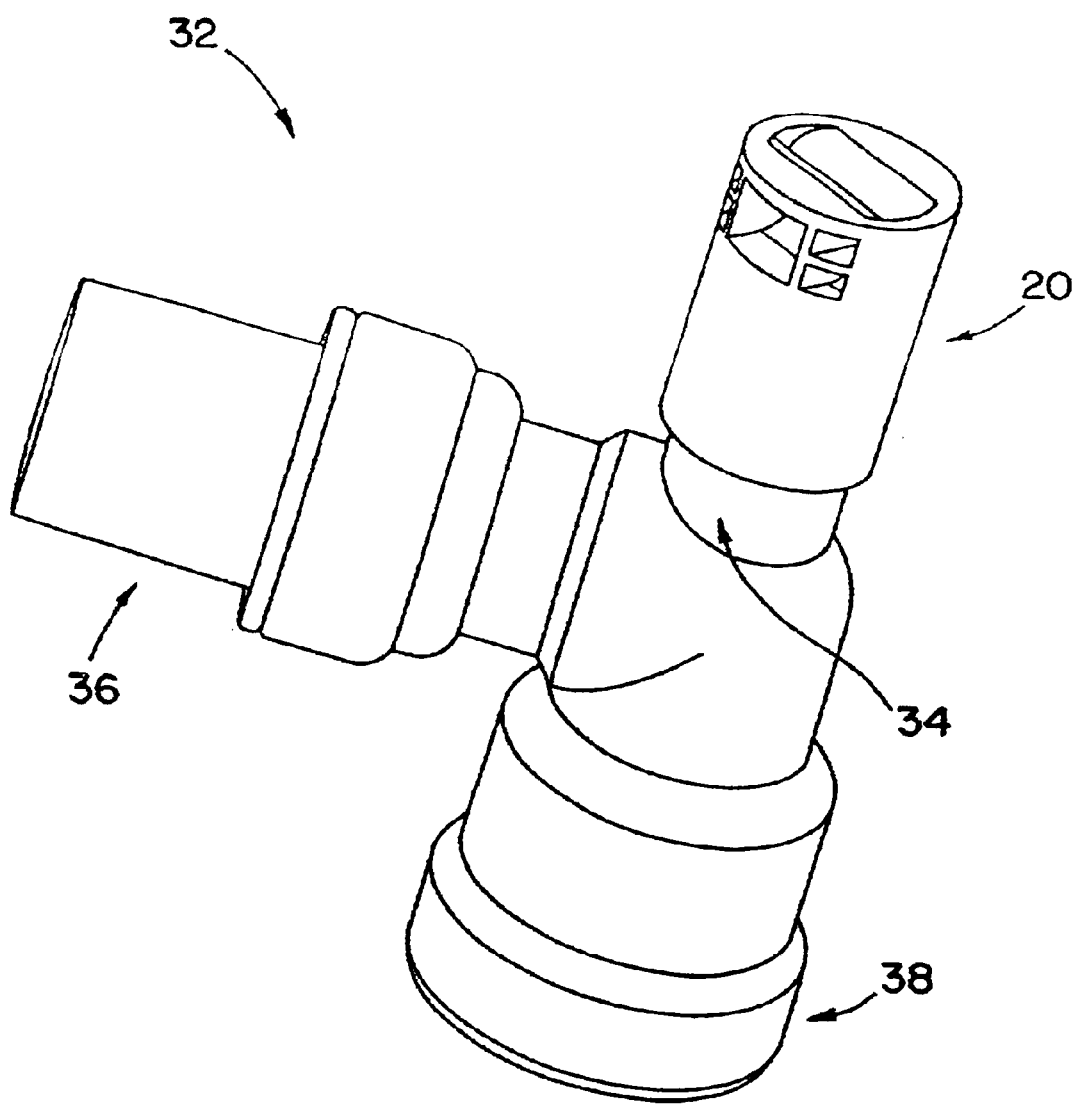
FIG. 2 is a perspective view of an access port closure valve of the present invention positioned on a T-shaped ventilator manifold that is used on a respiratory support system.

FIG. 2 shows a T-shaped manifold 32 with an access port 34 located in its elbow section. An access port closure valve 20 is shown attached to the access port 34. An aspiration and ventilation port 38 is attachable to a proximal port of an endotracheal tube or tracheostomy tube (not shown). Medical instruments such as bronchoscopes, catheters, sensor devices, or other medical instruments may be introduced to the patient through the access port closure valve 20, access port 34, and then through the aspiration and ventilation port 38. The T-shaped manifold 32 also has a ventilation port 36 attachable to a source of respiratory air.

It is to be understood that the access port closure valve 20 can be used on various manifolds known in the prior art, and not just those illustrated in the disclosed description.

Figure 3:
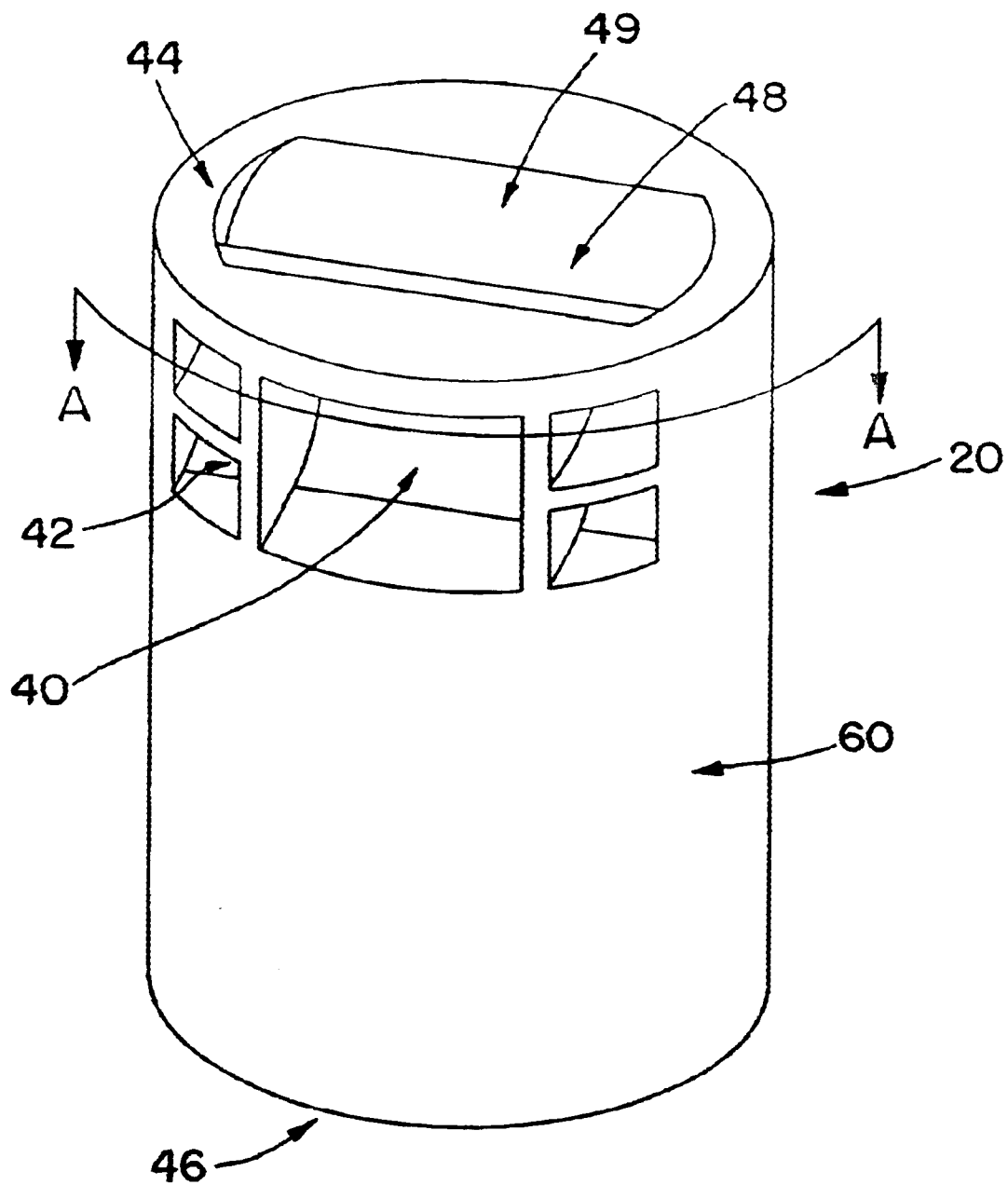
FIG. 3 is a perspective view of an access port closure valve of the present invention.

The access port closure valve 20 is shown in greater detail in FIG. 3. The access port closure valve 20 has a first end 46 that is frictionally fit onto the access port 34 in FIG. 2, and first access port 25 in FIG. 1. Such a frictional attachment also allows for the access port closure valve 20 to be readily removable from the access ports. However, it is to be understood that other forms of attachment known in the art may be used to attach the access port closure valve 20 onto the manifold 22. These could include, for instance, clips, adhesives, or sonic welding. The access port closure valve 20 also has a second end 44, which has an opening 48. Instrumentation is moved through the opening 48 of the second end 44, then through the access port closure valve 20, and exits the first end 46. A sealing member 49 is located within the opening 48. The access port closure valve 20 is provided with a cellular area 40 and a plurality of ribs 42. The purpose of these two features is to help shape the sealing member 49, improve the seal of the access port closure valve 20, strengthen the access port closure valve 20, and also provide for a surface with which to possibly attach other ports or instruments to the access port closure valve 20.

Figure 5:
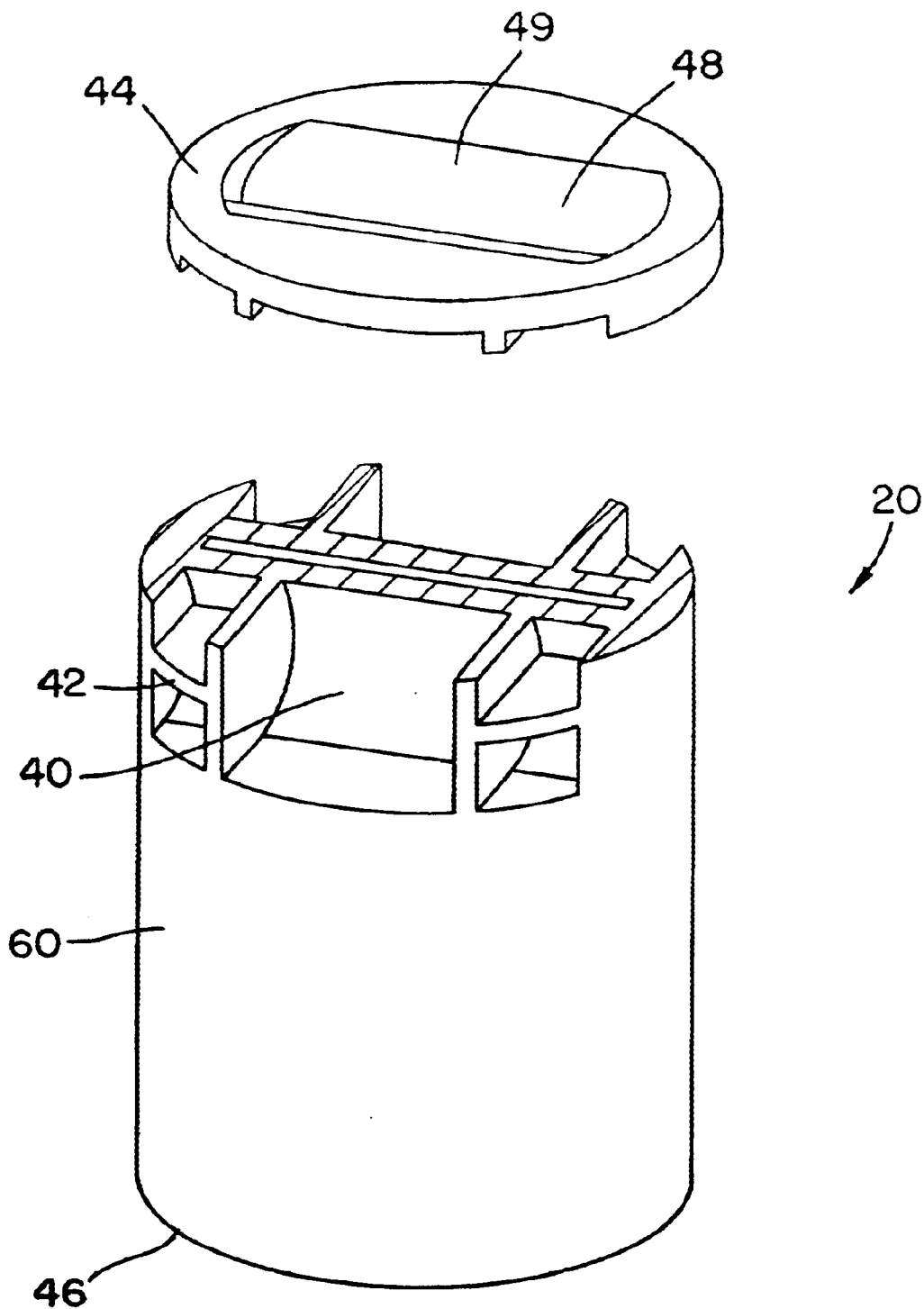
FIG. 5 is a perspective and cross-sectional view of the access port closure valve of FIG. 3 showing a cut along line A—A of FIG. 3.

FIG. 5 shows the access port closure valve 20 of FIG. 3 with a cut along line A—A of FIG. 3 and illustrates how the sealing member 44 is constructed when the access port closure valve 20 is molded as a single integral piece element. It is to be understood that the first end 46 and second end 44 are all a single integral piece, the cut out being necessary to show the detail of the plurality of ribs 42 and cellular area 40.

Figure 4A:
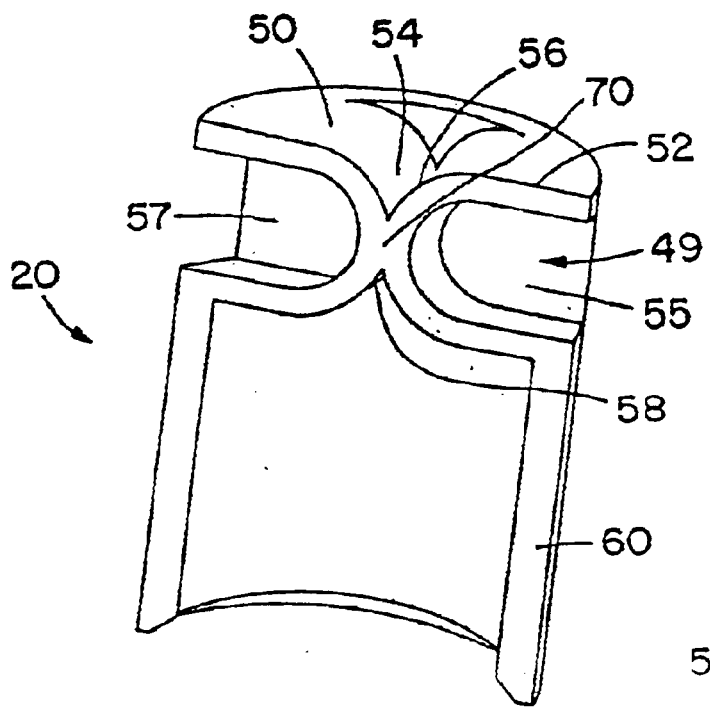
FIGS. 4A and 4B are cross sectional views of an alternate embodiment of an access port closure valve of the present invention.

FIG. 4A shows a cross-section of an access port closure valve 20 in accordance with the present invention and illustrates the operation of sealing member 49. A frame 60 is included and may be formed from any suitable rigid or semi-rigid material. The sealing member 49 is embedded within the frame 60 and includes a first sealing lip 50 and a second sealing lip 52. The first sealing lip 50 and second sealing lip 52 are shown having a U-shaped cross-section in FIG. 4A. However, it is to be understood that the first sealing lip 50 and second sealing lip 52 do not need to be of an exact circular cross-section. Other cross-sectional shapes are to be considered within the scope of the present invention. For instance, the lips 50 and 52 could be partially or fully cylindrical, as well as tubular and hollow.

FIG. 4A shows the first sealing lip 50 and the second sealing lip 52 in a closed position before the insertion of a suction catheter 62. It is to be understood however, that the access port closure valve 20 could be used with a different surgical instrument that is either semi-flexible, flexible, or rigid. The first sealing lip 50 and second sealing lip 52 define a pair of hollow cavities 57 and 55 respectively. Cavities 57 and 55 will change shape as the lips 50 and 52 are deformed as in FIG. 4B. The first sealing lip 50 and second sealing lip 52 are provided with a first sealing lip curved surface 54 and a second sealing lip curved surface 56. The first sealing lip curved surface 54 and second sealing lip curved surface 56 face one another and are urged into contact with one another in the closed position of sealing member 49. The curvature of the first sealing lip curved surface 54 and the second sealing lip curved surface 56 form a taper and a nip line 70 at the point of contact between the lips. The taper aids in the insertion of instruments into the access port closure valve 20.

The first sealing lip 50 and second sealing lip 52 are parallel to one another in orientation. A seal 58 is formed along the nip line between the first sealing lip curved surface 54 and the second sealing lip curved surface 56. As shown in FIG. 4A, seal 58 is a planar surface seal as opposed to a simple line seal along nip line 70. This is because the first and second sealing lips 50 and 52 are formed from a material capable of enough deformation to achieve a longitudinally extending planar seal. However, an embodiment of seal 58 being a line seal is to be considered within the scope of the present invention.

Figure 4B:
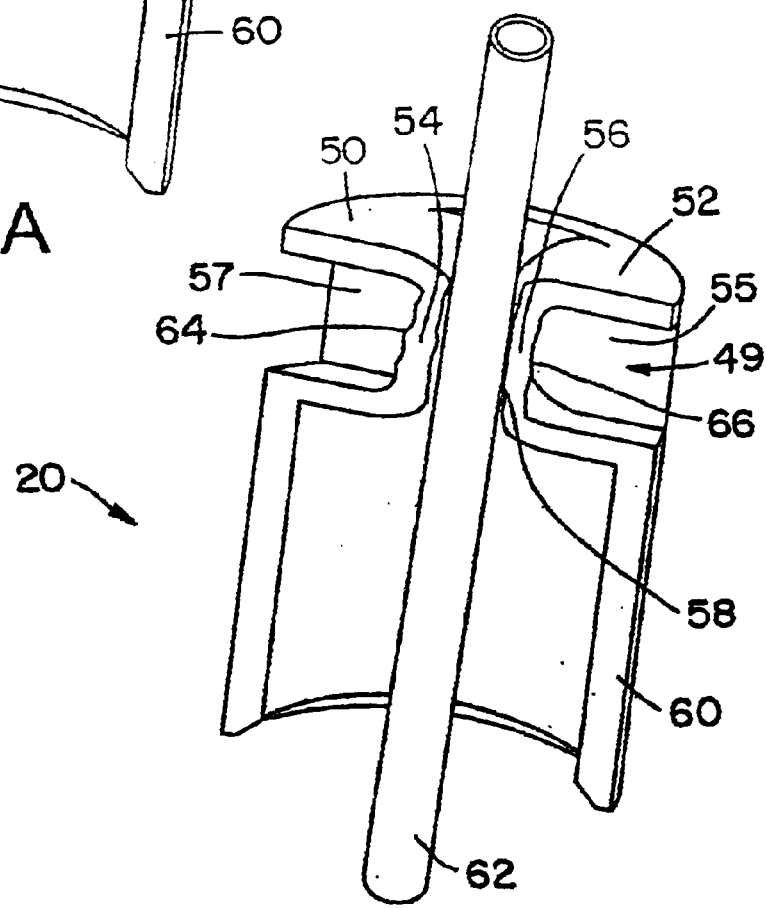

FIG. 4B shows a suction catheter 62 being inserted between the first sealing lip 50 and the second sealing lip 52 through the body of the access port closure valve 20. Insertion of the catheter 62 causes the sealing lips 50 and 52 to deform at locations 64 and 66 next to the insertion point of the suction catheter 62. The elastomeric properties of the sealing lips 50 and 52 cause the lips to separate and conform to the shape of the suction catheter 62 such that a seal 58 is formed about the suction catheter 62 as it is inserted between the sealing lips 50 and 52. Removal of the suction catheter 62 causes the first sealing lip 50 and the second sealing lip 52 to reform to the orientation shown in FIG. 4A.

It is to be appreciated that a retainer configuration such as the cellular area 40 and plurality of ribs 42 can be used on either one or both first sealing lip 50 and/or second sealing lip 52. Such embodiments are to be considered within the scope of the present invention. However, it is not necessary that sealing member 49 have the configuration of ribs 42 and cellular area 40 in order for the sealing member 49 to function.

The material used for the first sealing lip 50 and second sealing lip 52 is elastomeric and has exceptional shape memory to recover from the insertion of a device. For example, materials that could be used for the first sealing lip 50 and second sealing lip 52 include: styrenic thermoplastic elastomers, flexible polyvinyl chlorides (fPVC), and polyether block amide (a flexible nylon). The rest of the access port closure valve 20 can be made of these materials as well or a more rigid material.

The embodiment shown in FIG. 3 and FIG. 5 shows the first sealing lip 50 and the second sealing lip 52 formed integrally with the frame 60. The entire access port closure valve 20 is a single integrally molded part being made of the same material. It is to be understood that the first sealing lip 50 and second sealing lip 52 could be separate parts that are adhered to the walls of the frame 60 (for instance by sonic welding) or otherwise attached so that only the lips 50 and 52 are moveable relative to one another. The access port closure valve 20 can therefore be formed through various processes such as injection molding, material deposition, casting of thermoplastics or thermosets, or by multi-part assembly.

The access port closure valve of the present invention can be formed or permanently fixed in a respiratory support system, for example as a permanent component of an access port on respiratory support system manifold. The closure valve may also be provided as a separate component removably attachable to the manifold or other component on a respiratory support system.

It should understood that the invention includes various modifications that can be made to the embodiments of the access port closure valve described herein as come within the scope of the appended claims and their equivalents.

What is claimed is:

1. An access port closure valve for use with a respiratory support system comprising:
    a sealing member having a first and second sealing lip, the sealing lips are elongated and parallel to one another, the sealing lips are at least partially cylindrical in shape and are urged against one another and form a seal having a taper; and
    an elongated cylindrical frame that substantially surrounds the sealing member, the cylindrical frame and the sealing member being made of a same material, the sealing lips are disposed transversely across an end of the cylindrical frame, the cylindrical frame is configured to engage an access port of a respiratory support system, the sealing member seals the end of the cylindrical frame and accommodates passage of a surgical instrument through the cylindrical frame.

2. An access port closure valve according to claim 1, wherein the elongated cylindrical frame is frictionally attachable to a respiratory support system.

3. An access port closure valve according to claim 1, wherein the sealing member and the elongated cylindrical frame are formed by injection molding.

4. An access port closure valve for use with a respiratory support system comprising:
    a sealing member having a first and second sealing lip, the sealing lips are elongated and parallel to one another, the sealing lips are at least partially cylindrical in shape and are urged against one another and form a seal having a taper; and
    an elongated cylindrical frame that substantially surrounds the sealing member, the cylindrical frame and the sealing member being made of a same material, the sealing lips are disposed transversely across an end of the cylindrical frame, the cylindrical frame is configured to engage an access port of a respiratory support system, the sealing member seals the end of the cylindrical frame and accommodates passage of a surgical instrument through the cylindrical frame; and
    a plurality of ribs on each sealing lip, wherein the at least partially cylindrical shape of the first and second sealing lips is partially formed by the plurality of ribs.

5. An access port closure valve according to claim 4, wherein the sealing member and the elongated cylindrical frame are a single part.

6. An access port closure valve according to claim 5, wherein the sealing member and the elongated cylindrical frame are made of a material selected from the group consisting of styrenic thermoplastic elastomers, flexible polyvinyl chlorides, and polyether block amides.

7. An access port closure valve for use on an access port on a respiratory support system manifold comprising:
    a sealing member having a first and second sealing lip, the sealing lips are elongated and are parallel to one another, the sealing lips are at least partially cylindrical in shape and are urged against one another and form a seal having a taper, wherein the first and second sealing lips each define a hollow cavity; and
    an elongated cylindrical frame that substantially surrounds the sealing member, the cylindrical frame and the sealing member being made of a same material, the sealing lips are disposed transversely across an end of the cylindrical frame, the cylindrical frame is configured to engage an access port on a respiratory support system manifold, the sealing member seals the end of the cylindrical frame and accommodates passage of a surgical instrument through the cylindrical frame.

8. An access port closure valve according to claim 7, wherein the elongated cylindrical frame is configured to be frictionally attachable to a respiratory support system manifold.

9. An access port closure valve according to claim 7, wherein the sealing member and the elongated cylindrical frame are formed by injection molding.

10. An access port closure valve for use on an access port on a respiratory support system manifold comprising:
    a sealing member having a first and second sealing lip, the sealing lips are elongated and are parallel to one another, the sealing lips are at least partially cylindrical in shape and are urged against one another and form a seal having a taper; and
    an elongated cylindrical frame that substantially surrounds the sealing member, the cylindrical frame and the sealing member being made of a same material, the sealing lips are disposed transversely across an end of the cylindrical frame, the cylindrical frame is configured to engage an access port on a respiratory support system manifold, the sealing member seals the end of the cylindrical frame and accommodates passage of a surgical instrument through the cylindrical frame; and
    a plurality of ribs on each sealing lip, wherein the at least partially cylindrical shape of the first and second sealing lips is partially formed by the plurality of ribs.

11. An access port closure valve according to claim 10, wherein the sealing member and the elongated cylindrical frame are a single part.

12. An access port closure valve according to claim 11, wherein the sealing lips are made of a material selected from the group consisting of styrenic thermoplastic elastomers, flexible polyvinyl chlorides, and polyether block amides.

13. A respiratory support system comprising:
   a manifold having at least one port; and
   an access port closure valve engaging the port on the manifold, the access port closure valve comprising:
      a sealing member having a first and second sealing lip, the sealing lips are elongated and are parallel to one another, the sealing lips are at least partially cylindrical in shape and are urged against one another and form a seal having a taper; and
      an elongated cylindrical frame that substantially surrounds the sealing member, the cylindrical frame and the sealing member being made of a same material, the sealing lips are disposed transversely across an end of the cylindrical frame, the cylindrical frame is configured on the manifold port, the sealing member seals the end of the cylindrical frame and accommodates passage of a surgical instrument through the cylindrical frame.

14. A respiratory support system according to claim 13, further including a plurality of ribs on each sealing lip, wherein the at least partially cylindrical shape of the first and second sealing lips is partially formed by the plurality of ribs.

15. A respiratory support system according to claim 14, wherein the sealing member and the elongated cylindrical frame are a single part and are made from a same material.

16. A respiratory support system according to claim 15, wherein the sealing member and the elongated cylindrical frame are made of a material selected from the group consisting of styrenic thermoplastic elastomers, flexible polyvinyl chlorides, and polyether block amides.

17. A respiratory support system according to claim 13, wherein the elongated cylindrical frame is frictionally attached to the port on the manifold.

18. A respiratory support system according to claim 13, wherein the sealing member and the elongated cylindrical frame are formed by injection molding.

19. A respiratory support system according to claim 13, wherein the first and second sealing lips each define a hollow cavity.

20. A respiratory support system according to claim 13, wherein the cylindrical frame is permanently attached to the port on the manifold.

21. A respiratory support system according to claim 13, wherein the cylindrical frame is removably attached to the port on the manifold.

* * * * *